(12) United States Patent
Anderson et al.

(10) Patent No.: US 6,407,261 B1
(45) Date of Patent: Jun. 18, 2002

(54) PROCESS FOR PREPARING 4-HDYROXY INDOLE, INDAZOLE AND CARBAZOLE COMPOUNDS

(75) Inventors: Benjamin Alan Anderson, Zionsville; Nancy Kay Harn, Indianapolis, both of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/647,470

(22) PCT Filed: Apr. 15, 1999

(86) PCT No.: PCT/US99/08261

§ 371 (c)(1),
(2), (4) Date: Sep. 27, 2000

(87) PCT Pub. No.: WO99/54295

PCT Pub. Date: Oct. 28, 1999

Related U.S. Application Data

(60) Provisional application No. 60/082,109, filed on Apr. 17, 1998.

(51) Int. Cl.[7] .................... C07D 209/08; C07D 209/82
(52) U.S. Cl. ........................................ 548/440; 548/502
(58) Field of Search ................................. 548/440, 502

(56) References Cited

FOREIGN PATENT DOCUMENTS

| EP | 0 675 110 | 10/1995 |
|---|---|---|
| WO | WO 99 54300 | 10/1999 |

OTHER PUBLICATIONS

Ishibashi, et al., "New, Concise Route to Indoles Bearing Oxygen or Sulfur Substituent at the 4–Position. Synthesis of (±) and (S)–(–)–Pindolol and (±)–Chuangxinmycin," *Chem. Pharm. Bull.*, vol. 42, No. 5, pp. 271–276 (1994).

Wada, et al., "A Novel Synthesis of Quinazolinequinone and carbazolequinone through anionic cycloaddition: Its application to a synthesis of muaaryaquinone A," *Chem. Pharm. Bull.*, vol. 42, No. 2, pp. 416–418 (1994).

Remers, et al., "Synthesis of Indoles from 4–Oxo–4,5,6, 7–tetrahydroindoles II. Introduction of substituents into the 4 and 5 position," *J. Org. Chem.*, vol. 36, No. 9, pp. 1232–1240 (1971).

Ishibashi, et al., "A New, General Entry to 4–Substituted Indoles Synthesis of (S)–(–)–Pindolol and (±)–Chuangxinmycin," *Tetrahedron Letters*, vol. 34, No. 3, pp. 489–492 (1993).

Farrar, et al., "Useful Approach for Determination of the Structure of Organosulfur Compounds Sulfur–33 Highresolution FT–NMR," *J. Am. Chem. Soc.*, vol. 107, pp. 262–264 (1985).

Kobayashi, "Organic Sulfur Compounds VIII. The formation of sulfinate esters," *Bull. Chem. Jpn.*, vol. 39, No. 6, pp. 1296–1297 (1966).

Kobayashi, "Organic Sulfur Compounds III. The reactions of toluenesulfinic acid with acyl chlorides," *The Bull. Chem. Soc. Jpn.*, vol. 39, No. 5, pp. 967–970 (1966.)

*Primary Examiner*—Joseph K. McKane
*Assistant Examiner*—Sonya Wright
(74) *Attorney, Agent, or Firm*—Francis O. Ginah; Arleen Palmberg

(57) ABSTRACT

A process for preparing 4-hydroxy carbazoles useful as intermediates for preparing compounds that are useful for inhibiting sPLA$_2$ and novel intermediates.

2 Claims, No Drawings

PROCESS FOR PREPARING 4-HDYROXY INDOLE, INDAZOLE AND CARBAZOLE COMPOUNDS

This application is a 311 of PCT/US99/08261 filed Sep. 15, 1999, which claims benefit of U.S. Ser. No. 60/082,109 filed Apr. 17, 1998.

This invention relates to a process for preparing certain 4-hydroxy indole, indazole and 4-hydroxy carbozole compounds useful as intermediates for preparing compounds useful for inhibiting sPLA$_2$ mediated release of fatty acids for conditions such as septic shock.

Certain 1H-indole-3-glyoxamides are known to be potent and selective inhibitors of mammalian sPLA$_2$ useful for treating diseases, such as septic shock, adult respiratory distress syndrome, pancreatitis, trauma, bronchial asthma, allergic rhinitis, rheumatoid arthritis and related sPLA$_2$ induced diseases. EPO publication No. 0675110, for example, discloses such compounds.

Various patents and publications describe processes for making these compounds using 4-hydroxy indole intermediates.

The article, "Recherches en serie indolique. VI sur tryptamines substituees", by Marc Julia, Jean Igolen and Hanne Igolen, Bull. Soc. Chim. France, 1962, pp. 1060–1068, describes certain indole-3-glyoxylamides and their conversion to tryptamine derivatives.

The article, "2-Aryl-3-Indoleglyoxylamides (FGIN-1): A New Class of Potent and Specific Ligands for the Mitochondrial DBI Receptor (MDR)" by E. Romeo, et al., The Journal of Pharmacology and Experimental Therapeutics, Vol. 262, No. 3, (pp. 971–978) describes certain 2-aryl-3-indolglyoxylamides having research applications in mammalian central nervous systems.

The abstract, "Fragmentation of N-benzylindoles in Mass Spectrometry"; Chemical Abstracts, Vol. 67, 1967, 73028h, reports various benzyl substituted phenols including those having glyoxylamide groups at the 3 position of the indole nucleus.

U.S. Pat. No. 3,449,363 describes trifluoromethylindoles having glyoxylamide groups at the 3 position of the indole nucleus.

U.S. Pat. No. 3,351,630 describes alpha-substituted 3-indolyl acetic acid compounds and their preparation inclusive of glyoxylamide intermediates.

U.S. Pat. No. 2,825,734 describes the preparation of 3-(2-amino-1-hydroxyethyl)indoles using 3-indoleglyoxylamide intermediates such as 1-phenethyl-2-ethyl-6-carboxy-N-propyl-3-indoleglyoxylamide (see, Example 30).

U.S. Pat. No. 4,397,850 prepares isoxazolyl indolamines using glyoxylamide indoles as intermediates.

U.S. Pat. No. 3,801,594 describes analgesics prepared using 3-indoleglyoxylamide intermediates.

The article, "No. 565.—Inhibiteurs d'enzymes. XII.— Preparation de (propargylamino-2 ethyl)-3 indoles" by A. Alemanhy, E. Fernandez Alvarez, O. Nieto Lopey and M. E. Rubic Herraez; Bulletin De La Societe Chimique De France, 1974, No. 12, pp. 2883–2888, describes various indolyl-3 glyoxamides which are hydrogen substituted on the 6-membered ring of the indole nucleus.

The article "Indol-Umlagerung von 1-Diphenylamino-2, 3-dihydro-2,3-pyrrolidonen" by Gert Kollenz and Christa Labes; Liebigs Ann. Chem., 1975, pp. 1979–1983, describes phenyl substituted 3-glyoxylamides.

Many of these processes employ a 4-hydroxy indole intermediate. For example U.S. Pat. No. 5,654,326 U.S., herein incorporated by reference in its entirety, discloses a process for preparing 4-substituted-1H-indole-3-glyoxamide derivatives comprising reacting an appropriately substituted 4-methoxyindole (prepared as described by Clark, R. D. et al., Synthesis, 1991, pp 871–878, the disclosures of which are herein incorporated by reference) with sodium hydride in dimethylformamide at room temperature (20–25° C.) then treating with arylmethyl halide at ambient temperatures to give the 1-arylmethylindole which is O-demethylated using boron tribromide in methylene chloride (Tsung-Ying Shem and Charles A. Winter, Adv. Drug Res., 1977, 12, 176, the disclosure of which is incorporated by reference) to give the 4-hydroxyindole. Alkylation of the hydroxy indole is achieved with an alpha bromoalkanoic acid ester in dimethylformamide using sodium hydride as a base. Conversion to the glyoxamide is achieved by reacting the -[(indol-4-yl)oxy]alkanoic acid ester first with oxalyl chloride, then with ammonia, followed by hydrolysis with sodium hydroxide in methanol.

The process for preparing 4-substituted-1H-indole-3-glyoxamide derivatives, as set forth above, has utility. However, this process uses expensive reagents and environmentally hazardous organic solvents, produces furan containing by-products and results in a relatively low yield of desired product.

In an alternate preparation an appropriately substituted propronylacetate is halogenated with sulfuryl chloride. The halogenated Intermediate is hydrolyzed and decarboxylated by treatment with hydrochloric acid then reacted with an appropriately substituted cyclohexane dione. Treatment of the alkylated dione with an appropriate amine affords a 4-keto-indole which is oxidized by refluxing in a high-boiling polar hydrocarbon solvent such as carbitol in the presence of a catalyst, such as palladium on carbon, to prepare the 4-hydroxyindole which may then be alkylated and converted to the desired glyoxamide as described above.

This process however is limited by the required high temperature oxidation and requires recovery of a precious metal catalyst.

While the methods described above for preparing the 4-hydroxy indole intermediate are satisfactory, a more efficient transformation is desirable.

The present invention provides an improved process for preparing 4-hydroxy-indole intermediates. The process of the present invention can be performed with inexpensive, readily available, reagents under milder conditions. In addition, the present process allows for transformation with a wider variety of substituents on the indole platform. Other objects, features and advantages of the present invention will become apparent from the subsequent description and the appended claims.

The present invention provides a process for preparing a compound of the formula I

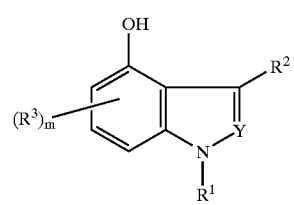

wherein:
Y is —CR$^4$ or —N—;
R$^4$ is H, —(C$_1$–C$_6$)alkyl or when taken together with R$^2$ forms a cyclohexeny ring $R^2$ is non-interfering substituent;
$R^3$ is a non-interfering substituent;
m is 1–3 both inclusive; and
$R^1$ is selected from groups (a), (b) and (c) where;
  (a) is —$(C_1-C_{20})$alkyl, —$(C_2-C_{20})$alkenyl, —$(C_2-C_{20})$alkynyl, carbocyclic radicals, or heterocyclic radicals, or
  (b) is a memeber of (a) substituted with one or more independently selected non-interfering substituents; or
  (c) is the group —(L)—$R^{80}$; where, (L)— is a divalent linking group of 1 to 12 atoms selected from carbon, hydrogen, oxygen, nitrogen, and sulfur; wherein the combination of atoms in —(L)— are selected from the group consisting of (i) carbon and hydrogen only, (ii) one sulfur only, (iii) one oxygen only, (iv) one or two nitrogen and hydrogen only, (v) carbon, hydrogen, and one sulfur only, and (vi) an carbon, hydrogen, and oxygen only; and where $R^{80}$ is a group selected from (a) or (b);

which process comprises oxidizing a compound of formula III

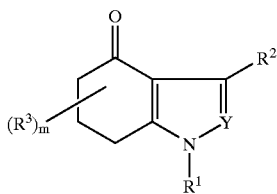

III by heating with a base and a compound of the formula

where R is —$(C_1-C_6)$alkyl or aryl and X is —$(C_1-C_6)$alkoxy, halo or —$OCO_2(C_1-C_6)$alkyl.

The invention provides in addition novel reagents of the formula

where R is —$(C_1-C_6)$alkyl, aryl or substituted aryl; and X is —$OCO_1$ $(C_1-C_6)$alkyl provided that when X is —$OCO_2CH_3$, R cannot be tolulyl.

The present invention provides, in addition novel intermediates of the formula

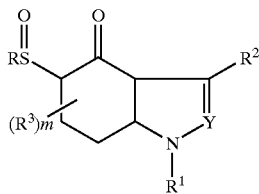

wherein:
R is —(C1–C6)alkyl, aryl or substituted aryl,
Y is —$CR^4$ or —N—;
$R^4$ is H, —$(C_1-C_6)$alkyl or when taken together with $R^2$ forms a cyclohexeny ring $R^2$ is non-interfering substituent;
$R^3$ is a non-interfering substituent;
m is 1–3; and
$R^1$ is selected from groups (a), (b) and (c) where;
  (a) is —$(C_1-C_{20})$alkyl, —$(C_2-C_{20})$alkenyl, —$(C_2-C_{20},)$alkynyl, carbocyclic radicals, or heterocyclic radicals, or
  (b) is a memeber of (a) substituted with one or more independently selected non-interfering substituents; or
  (c) is the group —(L)—$R^{80}$; where, (L)— is a divalent linking group of 1 to 12 atoms selected from carbon, hydrogen, oxygen, nitrogen, and sulfur; wherein the combination of atoms in —(L)— are selected from the group consisting of (i) carbon and hydrogen only, (ii) one sulfur only, (iii) one oxygen only, (iv) one or two nitrogen and hydrogen only, (v) carbon, hydrogen, and one sulfur only, and (vi) an carbon, hydrogen, and oxygen only; and
  where $R^{80}$ is a group selected from (a) or (b).

Such intermediates are useful for preparing compounds useful for inhibiting $sPLA_2$ mediated release of fatty acids for conditions such as septic shock.

Other objects, features and advantages of the present invention will become apparent from the subsequent description and the appended claims.

The compounds of the invention employ certain defining terms as follows:

As used herein, the term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl tert butyl, n-pentyl, isopentyl, neopentyl, heptyl, hexyl, octyl, nonyl, decyl, undecyl, dodecyl, tridecyl, tetradecyl and the like. The term "alkyl" includes —$(C_1-C_2)$alkyl, —$(-C_4)$alkyl, —$(C_1-C_6)$alkyl, —$(C_5-C_{14})$alkyl, and —$(C_1-C_{10})$alkyl.

The term "alkenyl" as used herein represents an olefinically unsaturated branched or linear group having at least one double bond. Examples of such groups include radicals such as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl as well as dienes and trienes of straight and branched chains.

The term "alkynyl" denotes such radicals as ethynyl, propynyl, butynyl, pentynyl, hexynyl, heptynyl as well as di- and tri-ynes. The term "$(C_1-C_{10})$ alkoxy", as used herein, denotes a group such as methoxy, ethoxy, n-propoxy, isopropoxy, n-butoxy, t-butoxy, n-pentoxy, isopentoxy, neopentoxyl, heptoxy, hexoxy, octoxy, nonoxy, decoxy and like groups, attached to the remainder of the molecule by the oxygen atom. The term $(C_1-C_{10})$alkoxy includes $(C_1-C_6)$alkoxy.

The term "halo" means fluoro, chloro, bromo or iodo.

The term "aryl" means a group having the ring structure characteristic of benzene, pentalene, indene, naphthalene, azulene, heptalene, phenanthrene, anthracene,etc. The aryl group may be optionally substituted with 1 to 3 substituents selected from the group consisting of $(C_1-C_6)$alkyl (preferably methyl), $(C_1-C_6)$alkoxy or halo (preferable fluorine or chlorine).

The term, "heterocyclic radical", refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyridyl, thienyl, fluorenyl, pyrrolyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, thianaphtheneyl, dibenzothiophenyl, indazolyl, imidazo(1.2-A)pyridinyl, benzotriazolyl, anthranilyl, 1,2-benzisoxazolyl, benzoxazolyl, benzothazolyl, purinyl, pryidinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, and quinoxalinyl.

The term "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, naphthyl, norbornanyl, bicycloheptadienyl, tolulyl, xylenyl, indenyl, stilbenyl, terphenylyl, diphenylethylenyl, phenylcyclohexeyi, acenaphthylenyl, and anthracenyl, biphenyl, bibenzylyl and related bibenzylyl homologues represented by the formula (bb),

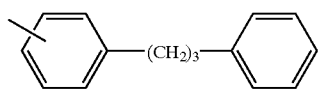

(bb)

where n is an integer from 1 to 8.

The term, "non-interfering substituent", refers to hydrogen, —($C_1$–$C_{14}$)alkyl, —($C_2$–$C_6$)alkenyl, —($C_2$–$C_6$) alkynyl, —($C_7$–$C_{12}$)aralkyl, —($C_7$–$C_{12}$)alkaryl, —($C_3$–$C_8$) cycloalkyl, —($C_3$–$C_8$)cycloalkenyl, phenyl, tolulyl, xylenyl, biphenyl, —($C_1$–$C_6$)alkoxy, —($C_2$–$C_6$)alkenyloxy, —($C_2$–$C_6$)alkynyloxy, —($C_1$–$C_{12}$)alkoxyalkyl, —($C_1$–$C_{12}$) alkoxyalkyloxy, —($C_1$–$C_{12}$)alkylcarbonyl, —($C_1$–$C_{12}$) alkylcarbonylamino, —($C_1$–$C_{12}$)alkoxyamino, —($C_1$–$C_{12}$) alkoxyaminocarbonyl, —($C_1$–$C_{12}$)alkylamino, —($C_1$–$C_6$) alkylthio, —($C_1$–$C_{12}$)alkylthiocarbonyl, —($C_1$–$C_6$) alkylsulfinyl, —($C_1$–$C_6$)alkylsulfonyl, —($C_1$–$C_6$) haloalkoxy, —($C_1$–$C_6$)haloalkylsulfonyl, —($C_1$–$C_6$) haloalkyl, —($C_1$–$C_6$)hydroxyalkyl, —($CH_2$)$_n$CN, —($CH_2$)$_n$NR$^9$R$^{10}$, —C(O)O($C_1$–$C_6$alkyl), —($CH_2$)$_n$O($C_1$–$C_6$ alkyl), benzyloxy, phenoxy, phenylthio; —(CONHSO$_2$)R$^{15}$, where R$^{15}$ is —($C_1$–$C_6$)alkyl; —CF$_3$, naphthyl or —($CH_2$)$_s$phenyl where s is 0–5; —CHO, —CF$_3$, —OCF$_3$, pyridyl, amino, amidino, halo, carbamyl, carboxyl, carbalkoxy, —($CH_2$)$_n$CO$_2$H, cyano, cyanoguanidinyl, guanidino, hydrazide, hydrazino, hydrazido, hydroxy, hydroxyamino, nitro, phosphono, —SO$_3$H, thioacetal, thiccarbonyl, furyl, thiophenyl —COR$^9$, —CONR$^9$R$^{10}$, —NR$^9$R$^{10}$, —NCHCOR$^9$, —SO$_2$R$^9$, —OR$^9$, —SR$^9$, CH$_2$SO$_2$R$^9$, tetrazolyl or tetrazolyl substituted with —($C_1$–$C_6$)alkyl, phenyl or —($C_1$–$C_4$)alkylphenyl, —($CH_2$)$_n$OSi($C_1$–$C_6$)alkyl and ($C_1$–$C_6$)alkylcarbonyl; where n is from 1 to 8 and R$^9$ and R$^{10}$ are independently hydrogen, —CF$_3$, phenyl, —($C_1$–$C_4$) alkyl, —($C_2$–$C_4$)alkylphenyl or -phenyl($C_1$–$C_4$)alkyl.

A preferred group of compounds of formula I prepared by the process of the instant invention are those wherein:

Y is CR$^4$ where R$^4$ is H or when taken together with R$^2$ forms a cyclohexenyl ring;

R$^3$ is H, —O($C_1$–$C_4$)alkyl, halo, —($C_1$–$C_6$)alkyl, phenyl, —($C_1$–$C_4$)alkylphenyl; phenyl substituted with —($C_1$–$C_6$)alkyl, halo, or —CF$_3$; —CH$_2$OSi($C_1$–$C_6$) alkyl, furyl, thiophenyl, —($C_1$–$C_6$)hydroxyalkyl, —($C_1$–$C_6$)alkoxy($C_1$–$C_6$)alkyl, —($C_1$–$C_6$)alkoxy ($C_1$–$C_6$)alkenyl; or —(CH$_2$)$_n$R$^8$ where R$^8$ is H, —CONH$_2$, —NR$^9$R$^{10}$, —CN or phenyl where R$^9$ and R$^{10}$ are independently hydrogen, —CF$_3$, phenyl, —($C_1$–$C_4$)alkyl, —($C_1$–$C_4$)alkylphenyl or -phenyl ($C_1$–$C_4$)alkyl and n is 1 to 8; and R$^1$ is H, —($C_5$–$C_{14}$)alkyl, —($C_3$–$C_{14}$)cycloalkyl, pyridyl, phenyl or phenyl substituted with from 1–5 substituents selected from the group consisting of —($C_1$–$C_6$)alkyl, halo, —CF$_3$, —OCF$_3$, —($C_1$–$C_4$)alkoxy, —CN, —($C_1$–$C_4$)alkylthio, phenyl($C_1$–$C_4$)alkyl, —($C_1$–$C_4$) alkylphenyl, phenyl, phenoxy, —OR$^9$; where R$^9$ and R$^{10}$ are independently hydrogen, —CF$_3$, phenyl, —($C_1$–$C_4$)alkyl, —($C_1$–$C_4$)alkylphenyl or -phenyl ($C_1$–$C_4$); tetrazole; tetrazole substituted with —($C_1$–$C_4$)alkyl or —($C_1$–$C_4$)alkylphenyl; or naphthyl.

The process of the present invention provides an improved method for synthesizing the compounds of formula I using inexpensive, readily available reagents as shown in Scheme I as follows.

Scheme I

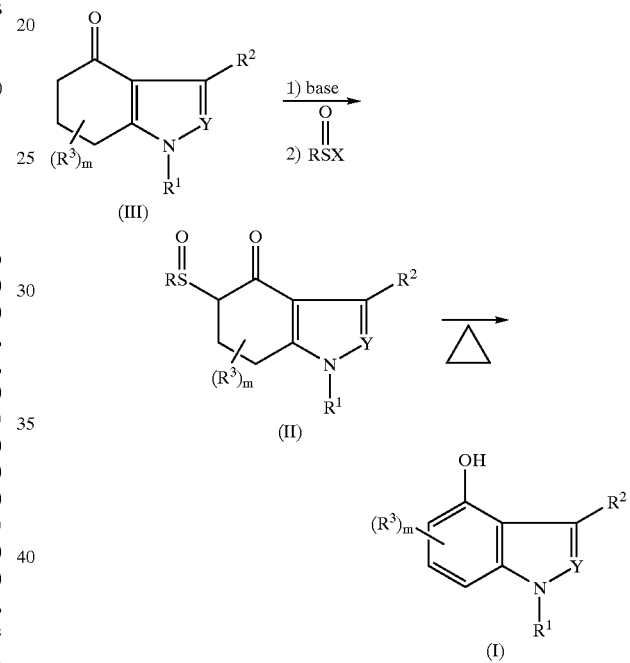

Ketone (III) is dissolved in a suitable solvent preferably an aprotic solvent such as THF. Other suitable solvents include but are not limited to DMF, dioxane, or toluene. The substrate/solvent solution may be sonicated or heated slightly, if necessary to facilitate dissolution.

The amount of solvent used should be sufficient to ensure that all compounds stay in solution until the desired reaction is complete.

The solution is treated with a base, preferably a strong base such as sodium hydride, then with a sulfinating agent of the formula

where R is —($C_1$–$C_6$)alkyl, aryl or substituted aryl and X is ($C_1$–$C_6$)alkoxy, halo or —OCO$_2$($C_1$–$C_6$)alkyl. The sulfinating reagent may be prepared according to the procedure of J. W. Wilt et al., J. Org. Chem, 1967, 32, 2097. Preferred sulfinating agents include methyl p-tolyl sulfinate, methylbenzene sulfinate or p-toluylsulfinic isobutyric anhydride.

Other suitable bases include but are not limited to LDA, sodium methoxide, or potassium methoxlde. Preferably two equivalents of base are used. Preferably, when sodium hydride is employed, the base is added before the sulfinating reagent. The order of addition of reagents is not important when sodium methoxide is used.

The reaction may be conducted at temperatures from about 25° C. to reflux, preferably at reflux and is substantially complete in from one to 24 hours.

The amount of sulfinating reagent is not critical, however, the reaction is best accomplished using a molar equivalent or excess relative to the starting material (III).

The above reactions may be run as a "one pot" process with the reactants added to the reaction vessel in the order given above, preferably with an acid quench of the base prior to reflux.

Dioxane is a preferred solvent in a "one part" process. THF and toluene, respectively, are preferred solvents if a "two pot" process is employed.

The intermediate (II) can be isolated and purified using standard crystalization or chromatographic procedures.

Standard analytical techniques such as TLC or HPLC can be used to monitor the reactions in order to determine when the starting materials and intermediates are converted to product.

In an alternate preparation, the sulfinating reagent can be replaced with a disulfide compound of the formula $R^{20}SSR^{20}$ where $R^{20}$ is alkyl or aryl. Oxidation of the sulfide intermediate can then be readily achieved using an appropriate oxidizing reagent such as hydrogen peroxide or m-chloroperbenzoic acid.

It will be readily appreciated by the skilled artisan that the starting materials for all of the above procedures are either commercially available or can be readily prepared by known techniques from commercially available starting materials. For example, when X is N, starting material (1) can be prepared according to the procedure of Peet, N. P., et al,. Heterocycles, Vol. 32, No. 1, 1991, 41.

When Y is —$CH_2R^4$, starting material V, is prepared according to the following procedure.

Scheme II

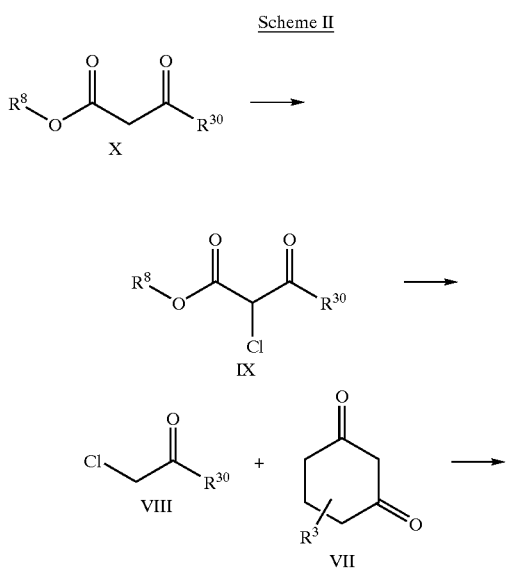

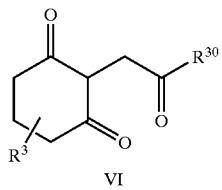

VI

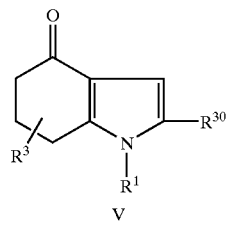

V $R^8$ is —$(C_1–C_6)$alkyl or aryl $R^{30}$ is H or —$(C_1–C_6)$alkyl

An appropriately substituted propionyl acetate X is first halogenated by treatment with sulfuryl chloride, preferably a. equimolar concentrations relative to the starting material, at temperatures of from about 0° C. to 25° C., preferably less than 15° C., to prepare IX.

Hydrolysis and decarboxylation of IX is achieved by refluxing with an aqueous acid, such as hydrochloric acid, for from about 1 to 24 hours. The solution containing the decarboxylated product VIII is neutralized to adjust the pH to about 7.0–7.5, then reacted with cyclohexanedione VII (preferably at equimolar concentrations) and a base, preferably sodium hydroxide, to yield the triketone monohydrate VI as a precipitate which may be purified and isolated, desired. The reaction is preferably conducted at temperatures of from −20° C. to ambient temperatures and is substantially complete in about 1 to 24 hours.

The above reactions are preferably run as a "one pot" process with the reactants added to the reaction vessel in the order given above. Preferably, the reaction is allowed to proceed without isolating compounds of formula IX or VIII, thus avoiding exposure to these volatile lachrymators.

Preparation of V is achieved by refluxing VI in a high boiling non-polar solvent which forms an azeotrope with water, preferably toluene, with an equimolar quantity of an amine of the formula $R^1NH_2$, where $R^1$ is as defined above. When $R^1$ is hydrogen, hexamethyldisilazane or ammonia may be used.

Solvents with a boiling point of at least 100° C. are preferred, such as toluene, xylene, cymene, benzene, 1,2-dichloroethane or mesitylene, thus eliminating the need for a pressure reactor. Sufficient solvent should be employed to ensure that all compounds stay in solution until the reaction is substantially complete in about 1 to 24 hours.

The following examples further illustrate the process of the present invention. The examples also illustrate the preparation of the intermediate compounds of this invention. The examples are illustrative only and not intended to limit the scope of the invention in any way.

Preparation 1

1-Benzyl-2-ethyl-4-oxo-4,5,6,7-tetrahydroindole

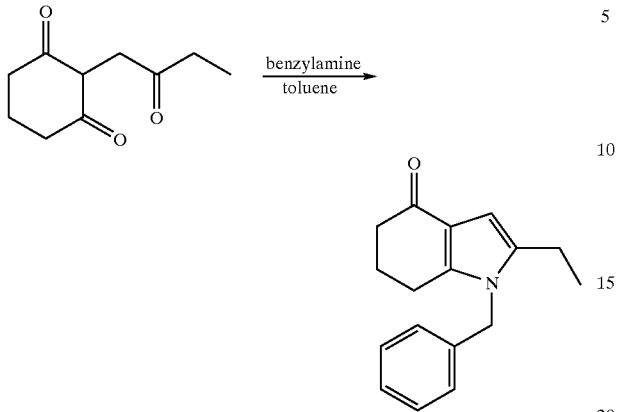

A. Preparation of 2-(2-oxobutyl)-1,3-cyclohexanedione

Methyl propionylacetate (130.15 g, 1.0 mol) is placed into a 2L Morton flask equipped with a mechanical stirrer, nitrogen inlet and thermocouple. External cooling is applied until the internal temperature is 10° C. Sulfuryl chloride (135 g, 1.0 mol) is added dropwise at a rate to maintain the temperature <15° C. When chromatographic analysis indicaets the total conversion to the desired chloro-compound 1M HCl (205 mL) is then added, and the reaction mixture is stirred at reflux for 18 hours. After cooling to room temperature, 4N NaOH is added to adjust the pH to 7.0 to 7.5. Cyclohexanedione (112.13 g, 1.0 mol) is added and the mixture is cooled in an ice bath. Then, 5N NaOH (200 mL, 1.0 mol) is added dropwise and the reaction is stirred for 18 hours at room temperature. The resulting thick precipitate is filtered, rinsed with water), and dried in vacuo to yield the subtitled triketone monohydrate.

B. Preparation of 1-Benzyl-2-ethyl-4-oxo-4,5,6,7-tetrahydroindole

The compound of Part A, above (1000 gms, 4.995 moles) was suspended in toluene (6000 ml, 6 vol). The mixture was warmed to 85° C. and stirred for 5 minutes. Benzylamine (562.6 gms, 5.25 moles, 1.05 eq) was added dropwise over about 30–45 minutes. Following the addition, the mixture turned to an amber colored solution. Heat was applied to the solution and water was azeotroped off until the reaction temperature reached 110° C. The reaction was allowed to stir at 110° C. for 2 hours at which time about 4000 mls of solvent was distilled off at atmospheric pressure. The solution was transferred to a Buchi flask and further evaporated to an amber viscous oil.

EXAMPLE 1

Preparation of 1-Benzyl-2-ethyl-4-hydroxyindole

The compound of Preparation 1 (0.5 g, 2 mmol) was dissolved in dioxane (2.5 mL). Sodium hydride (0.18 g, 4.5 mmol) was added. After 5 minutes, methyl benzenesulfinate (0.49 g, 3.2 mmol) was added. The mixture was warmed until the color changed to pink. The heat source was removed and the color of the mixture darkened from pink to red as gas evolution was observed. Thin layer chromatography indicated complete consumption of starting material (diastereomeric sulfoxides, $R_f$ 0.13, 0.19; 1/1 hexane/ethyl acetate). After 1 hour, dioxane (2.5 mL) was added, followed by acetic acid (0.26 mL, 4.5 mmol). The purple slurry was refluxed for 2 hours at which time the sulfoxides were no longer observed by thin layer chromatography. The reaction mixture was cooled to room temperature and diluted with chloroform. The solution was washed with saturated sodium bicarbonate solution, dried over anhydrous sodium sulfate and evaporated to give a red oil. Column chromatography with 10% ethyl acetate in hexane provided 0.39 g of a yellow solid. (79% yield)

Elemental Analysis for $C_{17}H_{17}NO$

| | | | |
|---|---|---|---|
| Theory: | C, 81.24, | H, 6.82, | N, 5.57 |
| Found: | C, 81.13, | H, 6.80, | N, 5.81. |

EXAMPLE 2

Preparation of 1-Benzyl-2-ethyl-4-hydroxyindole

A. The compound of Preparation 1 (0.5 g, 2 mmol) was dissolved in tetrahydrofuran (2.5 mL). Sodium hydride (0.18 g, 4.5 mmol) was added. After 5 minutes, methyl benzenesulfinate (0.49 g, 3.2 mmol) was added. After 15 minutes, the color of the mixture darkened to red as gas evolution was observed. The mixture was stirred for 1 hour. Thin Layer Chromatography indicated complete consumption of starting material (diastereomeric sulfoxides, $R_f$ 0.13, 0.19; 1/1 hexane/ethyl acetate). The reaction mixture was quenched with water, stirred for 5 minutes, and diluted with chloroform. The solution was washed with saturated sodium bicarbonate solution, dried over anhydrous sodium sulfate and evaporated to give a brown oil. The oil was dissolved in dioxane (5 mL) and refluxed for 2 hours at which time the sulfoxides were no longer observed by thin layer chromatography. The reaction mixture was cooled to room temperature and diluted with chloroform. The solution was washed with saturated sodium bicarbonate solution, dried over anhydrous sodium sulfate and evaporated to give a red oil. Column chromatography with 10% ethyl acetate in hexane provided 0.40 g of a yellow solid. (80% yield)

EXAMPLE 3

Preparation of 9-Benzyl-4-hydroxy-6-methoxy Carbazole

A. Preparation of 9-benzyl-4-hydroxy-6-oxy carbazole

A solution of N-benzyl anisidine (2.1 g, 11 mmol), 1,3-cyclohexadione (1.23 g, 11 mmol) and catalytic p-toluenesulfonic acid in 250 mL toluene was heated to reflux for 2 h with removal of water by codistillation. The resulting mixture was cooled to room temperature and concentrated. A dichloromethane solution of the residue was loaded on florisil and the product was eluted with a 1–3% methanol in dichioromethane. The eluent was concentrated and the resulting material (3.10 g) was dissolved in 250 mL acetonitrile. Palladium (II) acetate (2.7 g) was added and the mixture was heated to reflux for 2 h. The mixture was cooled and concentrated. A dichloromethane suspension of the mixture was loaded on florisil and the product was eluted with a 1–3% methanol in dichloromethane. Additional purification of the product was accomplished by silica gel chromatography (1–3% methanol in dichloromethane) to give 800 mg of the desired product. Recrystallization from dichloromethane/ethanol provided an analytically pure sample.

Elemental Analysis for $C_{20}H_{19}NO_2$:

| Calculated: | C, 78.66; | H, 6.27; | N, 4.59. |
|---|---|---|---|
| Found: | C, 78.90; | H, 6.34; | N, 4.55. |

B. Preparation of 9-benzyl-4-hydroxy-6-methoxy carbazole

The compound of part A, above (0.2 g, 0.65 mmol), was dissolved in tetrahydrofuran (2 mL). Sodium hydride (0.06 g, 1.5 mmol) was added. After 5 minutes, methyl benzenesulfinate (0.16 g, 1 mmol) was added. After 30 minutes, the brown mixture was warmed until gas evolution was sustained. The mixture became a thick paste. tetrahydrofuran (2 mL) was added and the resultant slurry was refluxed for 20 minutes. TLC indicated consumption of starring material (diastereomeric sulfoxides, $R_f$ 0.1, 0.14; 1/1 hexane/ethyl acetate). The reaction mixture was quenched with water, stirred for 5 minutes, and diluted with chloroform. The solution was washed with saturated sodium bicarbonate solution, dried over anhydrous sodium sulfate and evaporated to give an orange oil. The oil was dissolved in dioxane (5 mL) and refluxed for 1 hour at which time the sulfoxides were no longer observed by thin layer chromatography. The reaction mixture was cooled to room temperature and diluted with chloroform. The solution was washed with saturated sodium bicarbonate solution, dried over anhydrous sodium sulfate and evaporated. Column chromatography with 80% chloroform in hexane to 100% chloroform provided 0.13 g of an amber solid. (65% yield) Thin layer chromatography $R_f$ 0.27 (20% EtOAc in hexane);

Elemental Analyses for $C_{20}H_{17}NO_2$:

| Calculated: | C, 79.19; | H, 5.65; | N, 4.62; |
|---|---|---|---|
| Found: | C, 79.43; | H, 5.62; | N, 4.67. |

EXAMPLE 4

Preparation of 1-(3-Chlorophenyl(methyl))-4-hydroxyindole

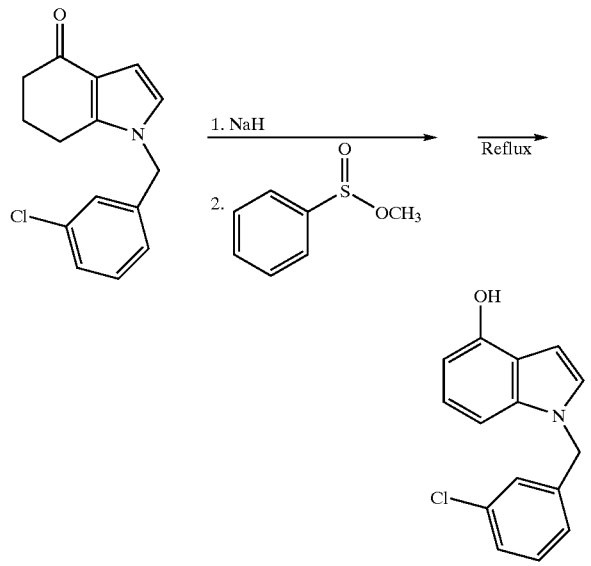

1-(3-chlorobenzyl)-4-oxo-4,5,6,7-tetrahydroindole was prepared from 1,5,6,7-tetrahydro-4H-indol-4-one and 3-chlorobenzylbromide using methodology common to the art. The pyrrole (0.5 g, 1.9 mmol) was dissolved in tetrahydrofuran (2.5 mL). Sodium hydride (0.18 g, 4.4 mmol) was added. After 5 minutes, methyl benzenesulfinate (0.48 g, 3.1 mmol) was added. The color of the mixture darkened to red as gas evolution was observed. The mixture was stirred for 1 hour. Thin layer chromatography indicated complete consumption of starting material (sulfoxides, $R_f$ 0.11; 1/1 hexane/ethyl acetate). The reaction mixture was quenched with water, stirred for 10 minutes, and diluted with chloroform. The solution was washed with saturated sodium bicarbonate solution, dried over anhydrous sodium sulfate and evaporated to give an orange oil. The oil was dissolved in dioxane (5 mL) and refluxed for 3 hours at which time the sulfoxides were no longer observed by thin layer chromatography. The reaction mixture was cooled to room temperature and a solution of lithium hydroxide (85 mg) in water (2 mL) was added. The solvent was evaporated and the residue was dissolved in chloroform. The solution was washed with saturated sodium bicarbonate solution, dried over anhydrous sodium sulfate and evaporated to give an orange oil. Column chromatography with 20% ethyl acetate in hexane provided 0.41 g of a yellow solid. (81% yield) TLC $R_f$ 0.28 (20% EtOAc in hexane); $^1$H NMR (CDCl$_3$): d 7.30 (d, J=8.2, 1 H), 7.24 (t, J=7.8, 1 H), 7.18 (s, 1 H), 7.11 (t, J=7.9, 1 H), 7.07 (d, J=3.2, 1 H), 6.98 (d, J=7.6, 1 H), 6.92 (d, J=8.3, 1 H), 6.75 (d, J=3.3, 1 H), 6.63 (d, J=7.6, 1 H), 6.01 (s, 1 H), 5.24 (s, 2 H).

Elemental Analyses for $C_{15}H_{12}NOCl$: Calculated: C, 69.91; H, 4.69; N, 5.43; Cl, 13.76. Found: C, 69.75; H, 4.64; N, 5.30; Cl, 14.05.

EXAMPLE 5

Preparation of 1-Phenyl-3-methyl-4-hydroxy Indazole

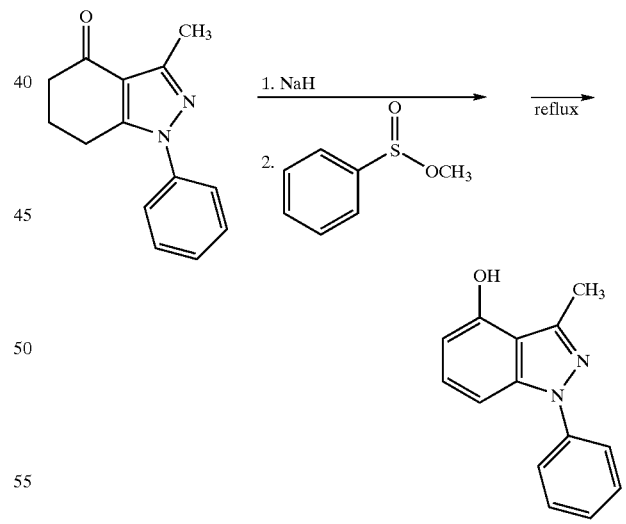

Starting material 1-phenyl-3-methyl-4-oxo-4,5,6,7-tetrahydroindazole (0.2 g, 0.9 mmol, prepared as described by Peet, N. P.; LeTourneau, M. E. *Heterocycles* 1991, 32, 41, was dissolved in tetrahydrofuran (2 mL). Sodium hydride (0.07 g, 1.6 mmol) was added. After 5 minutes, methyl benzenesulfinate (0.17 g, 1.1 mmol) was added. The color of the mixture changed to pink as gas evolution was observed. The mixture was stirred for 45 minutes. Thin layer chromatograhy indicated complete consumption of starting material (sulfoxides, $R_f$ 0.27, 0.33; 1/1 hexane/ethyl acetate). The reaction mixture was quenched with water, stirred for 1 hour, and diluted with dichloromethane. The solution was washed with saturated sodium bicarbonate solution, dried over anhydrous sodium sulfate and evaporated to give an orange oil. The oil was dissolved in dioxane (2 mL) and refluxed for 1 hour at which time the sulfoxides were no longer observed by TLC. The reaction mixture was cooled to room temperature and a solution of lithium hydroxide (38 mg) in water (2 mL) was added. The solvent was evaporated and the residue was dissolved in dichloromethane. The solution was washed with saturated sodium bicarbonate solution, dried over anhydrous sodium sulfate and evaporated to give an orange solid. Column chromatography with 20% ethyl acetate in hexane provided 0.14 g of a white solid. (70% yield) TLC $R_f$ 0.25 (20% EtOAc in hexane);

Elemental Analysis for $C_{14}H_{12}N_2O$:

| | Calculated: | C, 74.98; | H, 5.39; | N, 12.48; | O[001b], 7.13; |
|---|---|---|---|---|---|
| | Found: | C, 75.17; | H, 5.65; | N, 12.28; | O, 7.32. |

EXAMPLE 6

Preparation of 4-Hydroxy-9-methyl Carbazole

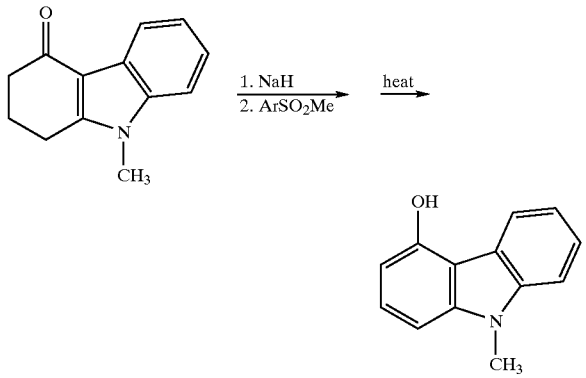

A suspension of 9-methyl-4-oxo-1,2,3,4-tetrahydrocarbazole (prepared by the methods described by Osuka, A.; Mori, Y.; Suzuki, H. *Chem. Lett.* 1982, 2031–2034; and Elz, S.; Heil, W. L. *Biorg. Med. Chem. Lett.* 1995, 5, 667). (0.20 g, 1.0 mmol) in 3 mL tetrahydrofuran was sonicated and heated to 50° C. Sodium hydride (60% dispersion in mineral oil; 0.07 g, 1.8 mmol) was added in one portion. Sonication and heating was continued for 1 hour and then methyl phenylsulfinate (0.2 g, 1.2 mmol) was added in one portion. The mixture was diluted after 3 hours with retrahydrofuran and water to give a homogenous solution. The solution was concentrated by rotary evaporation and the residue was partitioned between dichloromethane and water. The organic layer was washed with sodium bicarbonate and brine and then dried over magnesium sulfate, filtered and concentrated. The residue was Dissolved in dioxane and heated to reflux for 1 hour. The mixture was concentrated and partitioned between dichloromethane and water. The organic fraction was dried over magnesium sulfate, filtered and concentrated. The mixture was purified by silica gel chromatography (20% EtOAc, hexanes) to 0.075 g of the desired product (38%). TLC $R_f$=0.49 (20% ethyl acetate, hexanes); $^{13}$C NMR (CDCl$_3$) d 151.5, 142.6, 140.1, 126.0, 124.6, 122.4, 121.5, 118.8, 110.7, 107.7, 104.6, 101.0, 28.9; mass spectrum, m/z (FD, M$^{+1}$) 198.

EXAMPLE 7

Preparation of 1-Phenylmethyl-4-hydroxy-6-methyl Indole

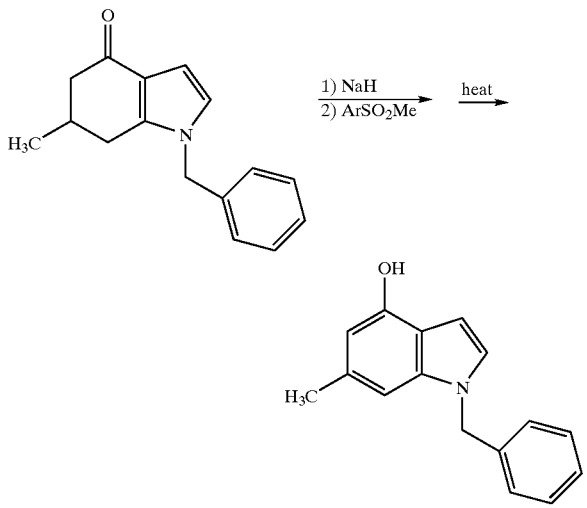

To a solution of the 1-phenylmethyl-4-oxo-6-methyl-4,5,6,7-tetrahydroindole (1.0 g, 3.5 mmol) in 5 mL tetrahydrofuran was added NaH (0.3 g, 7.5 mmol) in portions.

The resulting mixture was stirred 10 min and methyl phenylsulfinate (0.7 g, 4.5 mmol) was added in one portion. The mixture was stirred for 45 minutes and then warmed (35–45° C.) for 30 minutes. Water (5 mL) was added and the resulting mixture was stirred for 10 minutes. The intermediate sulfoxide was extracted with toluene. The tolurene solution was dried over sodium sulfate, filtered and concentrated to approximately 50 mL. The mixture was heated to reflux for 45 min. The solution was cooled to room temperature and washed with sodium bicarbonate and brine. The organic solution was dried over Na2SO4, filtered and concentrated to an oil. The residue was purified by silica gel chromatography (10% ethyl acetate in hexanes) to give 0.60 g of the desired product (60%).

What is claimed is:

1. A process for preparing a compound of the formula

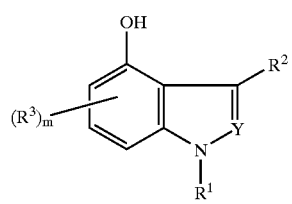

wherein:

Y is —CR$^4$,

R$^4$ is H, —(C$_1$–C$_6$)alkyl or when taken together with R$^2$ forms a cyclohexeny ring;

R$^2$ is a non-interfering substituent;

R$^3$ is a non-interfering substituent;

m is 1–3 both inclusive; and $R^1$ is selected from groups (a), (b) and (c) where;
- (a) is —$(C_1-C_{20})$alkyl, —$(C_2-C_{20})$alkenyl, —$(C_2-C_{20})$alkynyl, carbocyclic radicals, or heterocyclic radicals, or
- (b) is a memeber of (a) substituted with one or more independently selected non-interfering substituents; or
- (c) is the group —(L)—$R^{80}$; where, (L)— is a divalent linking group of 1 to 12 atoms selected from carbon, hydrogen, oxygen, nitrogen, and sulfur; wherein the combination of atoms in —(L)— are selected from the group consisting of (i) carbon and hydrogen only, (ii) one sulfur only, (iii) one oxygen only, (iv) one or two nitrogen and hydrogen only, (v) carbon, hydrogen, and one sulfur only, and (vi) an carbon, hydrogen, and oxygen only; and where $R^{80}$ is a group selected from (a) or (b);

which process comprises oxidizing a compound of formula III:

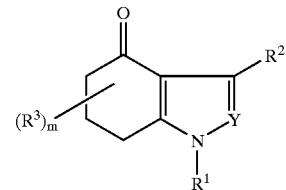

where Y, $R^1$, $R^2$ and $(R^3)_m$ are as defined above by heating with a base and a sulfinating reagent of the formula

where R is —$(C_1-C_6)$alkyl or aryl and X is —$(C_1-C_6)$alkoxy, halo or —$OCO_2(C_1-C_6)$alkyl.

2. The process of claim 1 where the sulfinating reagent is p-tolulylsulfinicisobutyric anhydride.

* * * * *

UNITED STATES PATENT AND TRADEMARK OFFICE
CERTIFICATE OF CORRECTION

PATENT NO. : 6,407,261 B1
DATED : June 18, 2002
INVENTOR(S) : Anderson et al.

It is certified that error appears in the above-identified patent and that said Letters Patent is hereby corrected as shown below:

<u>Title page,</u>
Item [54], Title, please delete "PROCESS FOR PREPARING 4-HDYROXY INDOLE, INDAZOLE AND CARBAZOLE COMPOUNDS" and replace with -- PROCESS FOR PREPARING 4-HYDROXY INDOLE, INDAZOLE AND CARBAZOLE COMPOUNDS --.

Signed and Sealed this

Twenty-sixth Day of November, 2002

Attest:

Attesting Officer

JAMES E. ROGAN
*Director of the United States Patent and Trademark Office*